(12) United States Patent
Kamiyama et al.

(10) Patent No.: US 8,393,199 B2
(45) Date of Patent: Mar. 12, 2013

(54) APPARATUS FOR MEASURING DIFFUSION OF TRANSDERMAL ABSORPTION PREPARATION

(75) Inventors: Fumio Kamiyama, Kyoto (JP); Ying-shu Quan, Kyoto (JP)

(73) Assignee: Cosmed Pharmaceutical Co., Ltd., Kyoto (JP)

( * ) Notice: Subject to any disclaimer, the term of this patent is extended or adjusted under 35 U.S.C. 154(b) by 698 days.

(21) Appl. No.: 12/525,305

(22) PCT Filed: Jan. 31, 2007

(86) PCT No.: PCT/JP2007/051597
§ 371 (c)(1),
(2), (4) Date: Aug. 20, 2009

(87) PCT Pub. No.: WO2008/093412
PCT Pub. Date: Aug. 7, 2008

(65) Prior Publication Data
US 2010/0071445 A1    Mar. 25, 2010

(51) Int. Cl.
*G01N 13/04* (2006.01)
(52) U.S. Cl. .................................... 73/64.47
(58) Field of Classification Search ............... 73/53.01, 73/64.47, 61.41, 61.43, 61.44, 61.45, 61.59, 73/61.75, 61.79, 64.53; 141/1
See application file for complete search history.

(56) References Cited

U.S. PATENT DOCUMENTS

| | | | |
|---|---|---|---|
| 5,183,760 A * | 2/1993 | Sweetana et al. | 435/284.1 |
| 5,198,109 A | 3/1993 | Hanson et al. | |
| 5,417,983 A * | 5/1995 | Nagase et al. | 424/487 |
| 5,500,416 A * | 3/1996 | Miyazawa et al. | 514/23 |
| 6,170,671 B1 | 1/2001 | Kitajima et al. | |
| 2003/0165429 A1 | 9/2003 | Takeoka et al. | |
| 2006/0034762 A1 | 2/2006 | Takeoka et al. | |
| 2006/0062730 A1 | 3/2006 | Takeoka et al. | |
| 2007/0190019 A1* | 8/2007 | Guo et al. | 424/78.05 |

FOREIGN PATENT DOCUMENTS

| | | |
|---|---|---|
| JP | 59-30038 A | 2/1984 |
| JP | 61-4745 U | 1/1986 |
| JP | 5-34556 U | 5/1993 |
| JP | 7-55686 A | 3/1995 |
| JP | 9-196911 A | 7/1997 |
| JP | 9-281112 A | 10/1997 |
| JP | 2001-174392 A | 6/2001 |

OTHER PUBLICATIONS

International Search Report for the Application No. PCT/JP2007/051597 mailed Mar. 27, 2007.

* cited by examiner

*Primary Examiner* — Peter Macchiarolo
*Assistant Examiner* — Tamiko Bellamy
(74) *Attorney, Agent, or Firm* — Cheng Law Group, PLLC (57) ABSTRACT

This invention is to provide a diffusion testing device to facilitate determination of diffusivity of prolonged release of drugs from transdermal therapeutic preparation.
The diffusion testing device is characterized by a receptor liquid reservoir; a diffusion testing cell having a receptor chamber functioning to be full of receptor liquid and within which a stirrer be placed, a receptor liquid supply unit, a thermostat bath to hold the diffusion testing cell, a stirring apparatus located beneath the thermostat bath to cause the rotation action of the stirrer set in the receptor chamber, a sampling unit permitting sampling and storage of receptor liquid dissolving permeated drugs. Said receptor liquid reservoir, said receptor chamber, said receptor liquid supply unit and said sampling unit are connected with each other via infusion tube. Said thermostat bath comprises aperturees or through-holes functioning to hold the diffusion testing cells, and metal block which has temperature regulation unit to be installed.

14 Claims, 8 Drawing Sheets

APPARATUS FOR MEASURING DIFFUSION OF TRANSDERMAL ABSORPTION PREPARATION

FIELD OF INVENTION

The present invention relates to a diffusion testing device for determination of permeation rate of drug from transdermal therapeutic preparation through skin.

BACKGROUND OF THE INVENTION

Franz cell is the commonly used test apparatus for studying of the transfer of a substance through a membrane. The Franz cell is in the form of a container with an upper half separated from a lower half by a membrane. In the upper compartment there placed a donor substance. The lower compartment is completely filled with a receptor media. The concentration of the testing substance in receptor solution is determined to study the diffusion rate of testing substance at a given time.

It is desired in clinical therapy to instantly understand the drug absorption from transdermal therapeutic preparation in human body when transdermal therapeutic preparation, such as nitroglycerin tape, ISDN tape, indomethacin gel, prednisolone ointment and so on, are applied. However, it is difficult to determine prolonged changes of drug diffusion rate just using said Franz diffusion cell.

Figure 1:
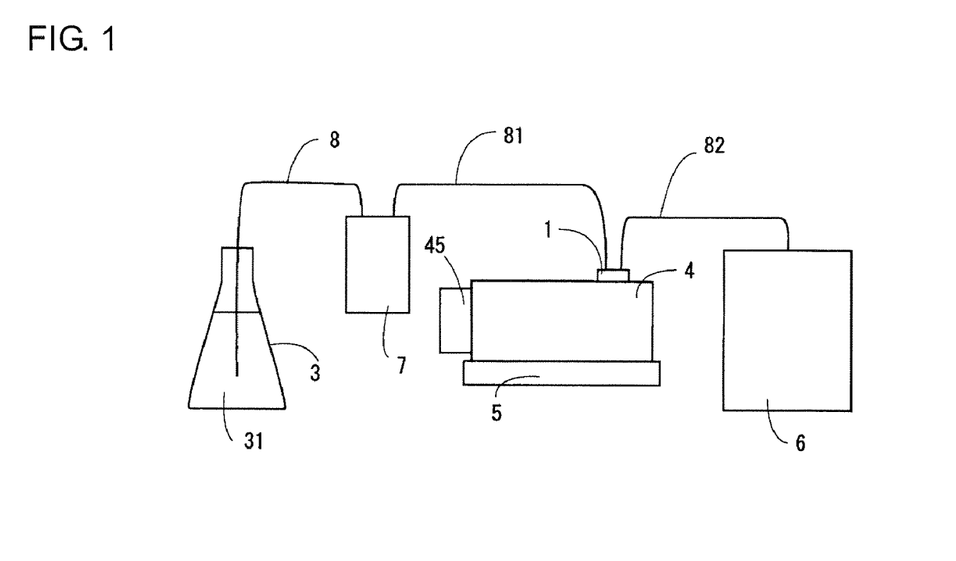
FIG. 1 is one example of the diffusion testing device in this invention.
Figure 15:
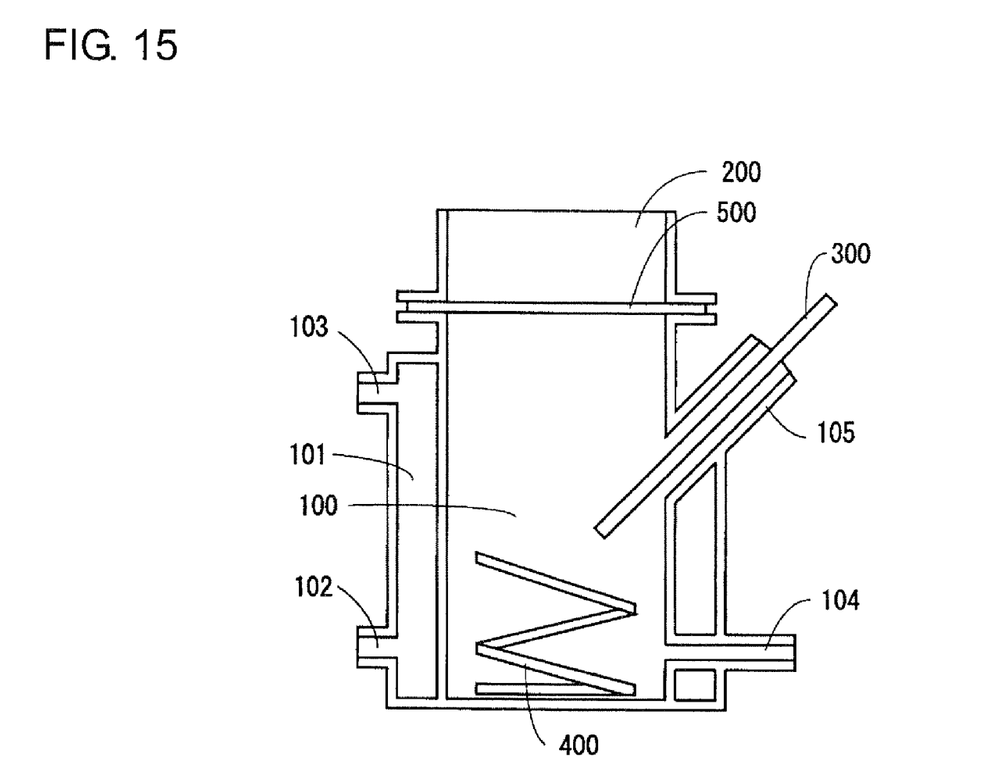
FIG. 15 is a sectional view of known diffusion cell.

In order to determine the permeation situation of the testing substance, the receptor solution have to be sampled at a given time. Therefore, a diffusion cell which is known as the Franz cell as shown in FIG. 1 was developed. FIG. 15 is the cross-sectional view of one of the examples of the diffusion cells developed.

100 is a cylindrical container defined by a flange on its top end. 200 is an upper container in shape of cylinder and fixed by a flange on its lower end. The container 100 is surrounded by a jacket 101 which has an inlet 102 and an outlet 103 integrally connected to the lower and upper wall of the jacket 101 respectively to supply and discharge of temperature-keeping liquid. Besides, a refilling port 104 for receptor media supply is connected to the lower wall of container 100. Connected to the middle wall of the container 100 is a branch shaped sample port 105 which has an internal sample tube 300 reaching at the near center of container 100 for sample-taking.

Using said diffusion cell to determine the transfer of the testing substance at any time, a stirrer 400 is firstly placed into the container 100. A membrane 500 is clamped between the flanges of container 100 and upper container 200. Then, the receptor media is supplied through the refilling port 104 to completely filling up container 100. Stirrer 400 is operated to cause the receptor liquid to be homogeneous.

Temperature-keeping liquid is to be supplied through the inlet 102 into jacket 101. A testing media is supplied into upper container 200 and in contact with membrane 500. At predetermined time interval, a known quantity of the receptor solution with permeated testing substance is removed through the sample tube 300 to determine the concentration of testing substance and additional quantity of fresh receptor media is supplied through refilling port 104 afterwards. (See references cited)

[Patent 1] U.S. Pat. No. 5,198,109

Although said diffusion cell can be used to determine the permeation of testing substance at any time, it is desirable to have the receptor solution maintained at a specifically known temperature level for 1 or several days when the permeation of testing substance in transdermal formulation to human body is studied. The way to achieve this is by supplying the liquid being at a pre-determined temperature through the inlet 102 to cause the circulation within the jacket 101 during the time. However, it is difficult to have the receptor liquid maintained at a specifically known temperature level for 1 or several days by this way.

Said diffusion cell may have to be immersed in a thermostatic water bath to finish the determination when there is no jacket 101 existed, resulting in difficult temperature control due to the water evaporation in water bath over a long time. In addition, volume of 3 to 10 ml of container 100 in said diffusion cell makes it difficult to keep the receptor liquid at a stable temperature over a long time.

DESCRIPTION OF THE INVENTION

The objective of the present invention is to provide a diffusion testing device so as to facilitate the determination of transdermal therapeutic of drugs from transdermal therapeutic preparation over a long time.

The diffusion testing device in this invention for permeation determination from transdermal therapeutic preparation is characterized by a receptor media reservoir; a diffusion testing cell including a receptor chamber functioning to be full of receptor solution and within which a stirrer be placed, a receptor liquid supply unit, a thermostat bath to hold the diffusion testing cell, a stirring apparatus located beneath the thermostat bath to cause the rotation action of the stirrer within the receptor chamber, a sampling unit permitting sampling and storage of receptor solution having permeated drugs. Said receptor media reservoir, said receptor chamber, said receptor media supply unit and said sampling unit are connected with each other via infusion tube. Said thermostat bath comprises aperturees functioning to hold the diffusion testing cells, through-holes and metal block which has temperature regulation unit to be installed.

Any diffusion cell for permeation rate determination may be used in said diffusion testing device, for example the diffusion cell in FIG. 15. Since the diffusion cell is placed in said thermostat bath to maintain a constant temperature in this invention, said diffusion cell with no jacket 110 surrounded can also be used in this invention.

Usually, when a diffusion cell is used to determine the permeation rate of the drug from transdermal therapeutic preparation, air bubble in the receptor media would frequently stay on the lower surface of the skin after the skin was clamped between the upper portion and lower portion of container 100 and receptor media is filled from the bottom of container 100. This results in an incorrect contacting area between skin and receptor liquid. Moreover, because removal of said air bubble takes both effort and time, it is difficult to test many of samples simultaneously.

Therefore, a diffusion cell which will be free form the above air bubble problem is desirable. To achieve this, it is desirable to have a diffusion testing cell (1) which comprises a cell which has an opening near the middle of the inside wall to be placed with skin and transdermal therapeutic preparation setting and a receptor chamber to be completely filled with receptor media, a cap to fix the skin and transdermal therapeutic preparation at said opening. Within said cell, a receptor liquid outlet connecting the receptor chamber from the upper part to outside of the cell and a receptor liquid inlet connecting the receptor chamber from the lower sidewall to outside of the cell bulk are to be constructed In order to determine the diffusivity of drugs from transdermal therapeutic preparation using said diffusion testing cell (1), cells will be placed in thermostat bath with the temperature maintained close to human or animal temperature and a plurality determinations will be progressed simultaneously. Therefore, it is desirable that the cell takes the form of cube or cuboids.

Said cap is used to fix the skin and transdermal therapeutic preparation at said opening and there is no any special limit to the cap. However, the skin and transdermal therapeutic preparation are flexible and deform easily at the opening. So, a holder to be used to fixedly hold the skin and transdermal therapeutic preparation in position and a cap, which can tightly clamp the holder, is preferred. Moreover, to clamp the holder easily and completely, a cap which can be screwed onto the sidewall of said cell is preferred.

Typical material for the cell bulk and cap (cap bulk and holder) can be any desired materials which is commonly utilized for diffusion testing cell, such as polyvinyl chloride resin, polymethyl methacrylate resin and polycarbonate resin etc. because of a better processability of these thermoplastic resins. It is desirable that said thermoplastic resin will not release any compound into receptor liquid. In addition, it is preferable to manufacture the cell bulk by transparent thermoplastic resin so that the receptor chamber, outlet and inlet are observable from outside.

Typical shape for the receptor chamber can be any desired shape. A desirable shape would be cylinder in trumpet which is narrowed gradually towards the outlet of receptor liquid so as to cause the drug concentration of the testing substance to be homogeneous in receptor liquid. Also, an opening is formed at the center sidewall of receptor chamber to set the skin and transdermal therapeutic preparation. Typical shape for said opening can be any desired shape, such as cylinder, ellipse or square etc.

Said skin can be any desired material usually used for study of permeation from transdermal formulation, for example, human skin, animal skin including rat skin, mouse skin, minipig skin, ape skin, snake skin, rabbit skin and marmot skin etc, synthetic human skin, dialysis membrane and silicon membrane etc.

The receptor chamber, receptor liquid outlet and receptor liquid inlet within the cell bulk can be manufactured by any known methods, for example, a aperture is to be designed through the cell bulk to set the receptor chamber, the outlet and the inlet.

Because said diffusion testing cell has to be place into a thermostat bath with the temperature near the body temperature to determine the diffusivity of the transdermal therapeutic preparation, it is desired to have the opening of the outlet and inlet to be located at the upper wall of the cell bulk.

A different and desirable diffusion testing cell (2) is comprising cell bulk with an opening at the upper sidewall to be placed with skin and transdermal therapeutic preparation and completely filling of receptor liquid, a collar to fix the skin at the opening, a cap to clamp the collar tightly at the opening and make a interspace between the cap and skin when the collar is fixed by the cap. Within the cell bulk, there forms a receptor liquid outlet forming from the upper of the receptor chamber through to the outside of the cell bulk and a receptor liquid inlet forming the lower part of the receptor chamber through to the outside of the cell bulk.

In order to determine the diffusivity of drugs from transdermal therapeutic preparation using said diffusion cell (2), cells will be placed into thermostat bath with the temperature maintained close to human or animal temperature and a plurality determinations will be progressed simultaneously. Therefore, it is preferred that the cell bulk takes the form of cube or cuboid.

Typical shape for the receptor chamber can be any desired shape. A desirable shape would be cylindrical which is narrowed gradually towards the receptor liquid outlet so as to cause the drug concentration of the testing substance to be homogeneous in receptor liquid. Also, an opening is formed on the upper sidewall of receptor chamber to set the skin and transdermal therapeutic preparation. Typical shape for said opening can be any desired shape, such as cylinder, ellipse or square ect.

Said collar is used to fix the skin and transdermal therapeutic preparation at the opening. Then the collar is clamped by a cap to completely fix the skin and transdermal therapeutic preparation at the opening. To form an inter-space between the skin and transdermal therapeutic preparation and the cap when the skin is fixed by the cap at the opening, the collar is designed with a through-hole shape which has the similar form of the opening of receptor chamber.

Said cap is used to clamp the collar to have the completely fixed at the opening. When the skin is fixed at the opening with the collar, an inter-space is formed between the skin and the cap. So, there is no any typical limitation to the cap. Transdermal therapeutic preparation which may comprise a liquid is placed into the inter-space and the diffusivity of the preparation can be determined using this diffusion cell.

Usually, liquid transdermal therapeutic preparation is provided after the skin is fixed at the opening, it is desirable that the cap is designed with a through-hole and comprises a holder to press the collar and a cell bulk which can be inserted into said through-hole. In order to easily and completely press the collar, it is desirable that the holder can be screwed onto the upper sidewall of the cell bulk and the through-hole of the holder takes the similar shape of the opening of receptor chamber. Moreover, it is desirable that when liquid percutanesou absorption preparation is to be place into the dent which is formed between the skin and collar (and the holder), the cell bulk have to be carefully inserted into the through-hole of the holder to make sure there is no air to be trapped into the inter-space and thereafter a liquid layer of transdermal therapeutic preparation is to be formed. Therefore, a cap bulk attached with through-hole connected through top and bottom of the cell bulk is desirable so as to smoothly remove the air and the extra liquid transdermal therapeutic preparation.

Typical material and manufacturing method for said cell bulk, collar and cap (cap bulk and holder) are the same as said diffusion cell (1). However, the test is conducted by placing the diffusion cell into a thermostat bath with the temperature near the body temperature to determine the diffusivity of drug from the transdermal therapeutic preparation. So it is desirable that both the openings of the receptor liquid outlet and the receptor liquid inlet are to be located at the upper wall of the cell bulk.

Furthermore, a different and desirable diffusion testing cell (3) is comprising a cell bulk with an opening at its upper sidewall to fix the skin and percutaneous preparation and a receptor chamber functioning to be completely filling of receptor liquid, a collar functioning to temporarily fix the skin and transdermal therapeutic preparation at the opening and a cylindrical cap which is to be clamped onto the collar to the opening to fix the collar. Two openings are designed at the t upper and lower side of the receptor chamber. Within the cell bulk, a receptor liquid outlet is designed from the upper part of the receptor chambers to outside of the cell bulk and the receptor liquid inlet is designed from the lower sidewall of the chamber.

The receptor chamber is divided into upper and lower chambers with the upper part being bisected into first upper receptor chamber and second upper receptor chamber by a partition board. There are openings formed at top of the first and second upper receptor chambers so as to be placed with the skin and transdermal therapeutic preparation.

Typical shape for the lower receptor chamber can be any desired shape. A desirable shape would be cylindrical so as to cause the drug concentration of the testing substance to be homogeneous in receptor liquid. The combined chamber shape of first and second upper receptor chambers is preferred to be the same as that of the lower receptor chamber. It is desirable that bisection of the upper receptor chamber by the partition board is symmetrical. Although there is no special limit to the height of the partition board, a too lower or too higher partition board will respectively not reach the effect of section and not homogeneously mix the receptor liquid. Therefore, the height of the aperture head is preferably 10% to 50% of that of the receptor chamber. Typical shape for said opening can be any desired shape, such as cylinder, ellipse or square etc.

Said collar is used to temporarily fix the skin (and transdermal therapeutic preparation) at the opening. Then the collar is pressed by a cap to fix the skin and transdermal therapeutic preparation at the opening. In addition, within the collar, two through-holes corresponding to each opening which is designed at the top of the first and second upper receptor chambers respectively are constructed. When the skin and transdermal therapeutic preparation are fixed by the cap, the transdermal therapeutic preparation will be emerged in the cylindric part of the cap.

Said cap is used to press the collar to fix the skin and transdermal formulation at the opening. After the skin and transdermal formulation are fixed through the collar by the cap, two through-holes of the collar forms two cylinder. Moreover, for easily and completely clamping of the holder at the opening by the cap, it is desirable that cap can be screwed onto the sidewall of the cell bulk.

Typical material and manufacturing method for said cell bulk, collar and cap are the same as said diffusion cell. Since the diffusion cell (3) is placed into a thermostat bath with the temperature near the body temperature to determine the diffusivity of drug from the transdermal therapeutic preparation, it is desirable that openings of the receptor liquid outlet and the receptor liquid inlet are located at upper wall of cell bulk.

Said diffusion cell (3) is applicable when iontophoretic transdermal permeation is progressed. Iontophoresis is a method of propelling charged drug through the skin by a low electrical current. Two parts of the fixed transdermal therapeutic preparation at two openings are connected with the electrodes through cap cylinder. Then the diffusivity of transdermal therapeutic preparation can be determined by iontophoretic method under current.

In order to supply the receptor liquid into diffusion testing cell (receptor chamber) and then to supply the receptor liquid in diffusion testing cell (receptor chamber) to sampling device, in this invention, receptor liquid reservoir, receptor chamber, receptor liquid supply unit and sampling device, are designed to be connected each other via infusion tube.

It is desirable that the order of connection by the infusion tube is as follows: receptor liquid reservoir, receptor liquid supply unit, receptor chamber and sampling device. In this case, receptor liquid is aspirated from reservoir to the supply unit, then from the supply unit to receptor chamber, and finally from receptor chamber to the sampling device.

Another different and desirable connection order via the infusion tube is as follows: receptor liquid reservoir, receptor chamber, receptor liquid supply unit, and sampling device. In this case, receptor liquid in reservoir is supplied to supply unit via receptor chamber, and then receptor liquid is aspirated from the supply unit to sampling device.

Within the diffusion testing cell, it is desirable that a watertight connection of infusion tube with either the outlet or inlet of receptor liquid is easily and completely reached. So spiral grooves are threaded at both of the opening of receptor liquid outlet and receptor liquid inlet. There is a junction unit at the end of the infusion tube which can be water-tightly screwed.

An infusion tube with smaller radii is desirable because larger radii may cause permeated drug in receptor liquid within the receptor chamber to be diffused to the receptor liquid in tube which would result in a lower determination precise. The tube normally has a internal radius in the range of 0.2 mm to 5 mm, preferably 0.5 mm to 2 mm. In addition, a longer infusion tube may cause a large amount of receptor liquid to be infused to receptor chamber when receptor liquid with permeated drug is infused to sampling device. The drug concentration of receptor solution in receptor chamber will be diluted and the determination precise will be lower. So a shorter infusion tube is desirable. The infusion tube usually has a length in the range of 20 cm to 100 cm, preferably 30 cm to 50 cm.

Although there is no typical limit to said receptor liquid supply unit for drawing receptor liquid from receptor liquid reservoir to diffusion testing cell, it is necessary that a precise volume of receptor liquid is withdrawn at a given time. Therefore, a pump which can withdraw receptor liquid quantitatively is desirable.

It is also desirable that a plurality of determination can be processed simultaneously. So, within the diffusion testing device for determination of transdermal therapeutic formulation, one supply unit device for receptor liquid is connected to one diffusion testing cell, and a plurality of diffusion testing cells to be set up at one time is preferred.

Receptor liquid sampling device is a device to sample and reserve the receptor liquid so as to determine the concentration change of the permeated drug with time. The sampling device has a similar working mechanism as that of the fraction collector. Said sampling device is used to firstly reserve the infused receptor liquid with permeated drug into the sample cell and then supply it to a device for concentration determination (eg. higher performance liquid chromatography, HPLC; gas chromatography, GC). For example, the sample cell with the said infused receptor liquid in it is placed into the HPLC sample holder and the drug concentration is determined.

Said thermostat bath comprises apertures to have a diffusion testing cell been placed into, through-hole and metal block which have the temperature regulation device installed. Said metal block may be either a metal chunk or bed of metal plates. Typical material for metal can be any desired metal, such as iron, stainless steel, aluminium etc. However, it is desirable to use aluminum for its lightweight, excellent formability and better rusting prevention.

Typical shape for aperture and through-hole can be any desired shape. Because the aperture is used to hold the diffusion testing cell and to keep the cell at a known temperature level, it is desired that said aperture takes almost the same shape as that of the diffusion testing cell. Since diffusion testing cell usually takes the shape of cube or cuboids, it is preferably that the aperture to be in shape of cuboids. Also it is preferred that the aperture and the through-hole can be designed for a plurality of diffusion determinations.

Said temperature regulation device can be any known temperature regulation device. For example, the temperature regulation device can be a thermostat temperature regulator which has planar heater or string heater to be installed interiorly and surrounded of the metal block. Another temperature regulation device can be a circulation system by the circulation action of the water and oil maintained at a known temperature in the pipes which located interiorly and surrounded of the metal block.

The stirring unit is to be located beneath the thermostat bath. The stirring unit can be any known unit to rotate the stirrer within the receptor chamber. If a plurality of aperturees and through-holes are designed in the thermostat bath, the diffusion testing cell is placed into each aperture and through-hole. Therefore, it is desired that each aperture and through-hole has a corresponding stirring unit. Integrally 6 and 12 consecutive connection of the stirring unit is preferred.

The testing method of diffusivity of drug from transdermal therapeutic formulation with the diffusion testing device in this invention is to be explained when the diffusion testing cell (1) is applied.

Firstly, a stirrer is placed into the receptor chamber. The diffusion testing cell is installed with the opening upwards. The skin and transdermal therapeutic formulation are tightly held in position by the cap at the opening with the skin facing the receptor chamber.

If transdermal therapeutic formulation is in form of adhesive tape, it may paste onto the skin directly. When formulation with fluidity, such as gel, ointment and jell, are applied, it is better to apply them onto the skin before setting the skin to the apparatus.

The skin and transdermal therapeutic formulation placed at the opening is covered by the collar for a temporary fix. Then the cap bulk is clamped onto the collar to completely fix the skin and the transdermal therapeutic preparation. Because the skin and transdermal therapeutic formulation is temporarily fixed by the collar, rumple will not be appeared when the cap bulk is screwed onto the sidewall of the cell bulk.

Next, the diffusion testing cell (1) is placed into the aperture or the through-hole of metal block of the thermostat bath with the skin and tranderrmal therapeutic formulation in a vertical attachment. The receptor chamber is completely filled with receptor liquid. In other words, the diffusion testing cell (1) is placed into the aperture of metal block of the thermostat bath with the top-wall of the cell bulk upwards. It is desired that receptor chamber can be completely filled with receptor liquid simultaneously from receptor liquid supply unit when a plurality of diffusion cells are used.

Before the diffusion testing cell is placed into thermostat bath, it is desired that both the receptor liquid supply unit and receptor liquid inlet of the diffusion testing cell, receptor liquid outlet of the diffusion testing cell and sampling device are to be connected by the infusion tube, respectively.

Since the skin and transdermal therapeutic formulation are attached vertically, air bubbles will not be trapped at the surface of the skin when receptor liquid is completely filled. If air bubble is trapped at the surface of the skin, it would be possible to remove the air bubble by just shaking the diffusion cell.

Then, within the thermostat bath, the stirrer is magnetically rotated to cause the receptor liquid to be maintained at a specifically known temperature level. Drug in the transdermal therapeutic formulation is permeated to the receptor liquid. To test the diffusion rate of the drug in transdermal therapeutic formulation, it is desired that receptor liquid to be maintained at the same temperature as the object to which the preparation will be applied. The stirring action of the stirrer in the receptor chamber causes the drug concentration of the receptor liquid to be homogeneous. Generally, the stirring action of the stirrer is caused by the stirring device installed beneath the receptor chamber (diffusion testing cell, thermostat bath).

Then, with the infusion of receptor liquid into the receptor chamber at predetermined time (usually 1 to 4 hours), receptor solution with permeated drug is infused into the receptor liquid distribution device to distribute into the sample cell and then stored for later use.

When receptor liquid to be infused into the receptor chamber in order to begin the determination experiment, the receptor liquid remained in the infusion tube on the side of the outlet have to be firstly infused. If the receptor liquid which is to be infused into the receptor chamber is in a small amount, the receptor liquid in the receptor chamber can not be withdrawn. So that a large amount of receptor liquid to be infused into the receptor chamber will dilute the concentration of drug in receptor liquid and result in a lower determination precise. Therefore, it is desired that the amount of receptor liquid to be infused into the receptor chamber at one time is to be 0.05 cm$^2$ to 2.0 cm$^2$, more preferably 0.1 to 1.0 cm$^2$.

In addition, when the receptor liquid is infused into the sampling device and then distributed into the sample cell, the liquid which to be infused into the sample cell firstly is, not the liquid which has the same concentration as the liquid in the receptor chamber, but the liquid remained in the infusion tube on the side of outlet channel. Therefore, a total volume of liquid in infusion tube on the side of the outlet has to be discharged before liquid to be distributed into the sample cell.

Next, the testing method of diffusivity of drug from transdermal therapeutic formulation with the diffusion testing device in this invention is to be explained when said diffusion testing cell (2) is applied.

Firstly, a stirrer is placed into the receptor chamber. The diffusion testing cell (2) is installed with the opening upwards. The skin is placed at the opening and then covered with a collar for temporary fixing. Then, a liquid transdermal therapeutic preparation is supplied into the space which is formed between the skin and the collar. The skin and collar are fixed with the cap and a liquid transdermal therapeutic preparation layer is formed. Because the skin and transdermal therapeutic formulation is temporarily fixed by the collar, rumple will not be appeared when the cap is screwed onto the sidewall of the cell bulk.

If the cap comprises a cap bulk and a holder, the liquid transdermal therapeutic preparation is supplied onto the skin after the skin and collar are fixed by the holder. Then the cell bulk is to be inserted into the through-hole of the holder to form a liquid transdermal therapeutic preparation layer. If the cap bulk has a through-hole, when an excess amount of transdermal therapeutic preparation is to be supplied, the excess liquid preparation can be removed from the through-hole after the cell bulk insert into the through-hole of the holder, and then the interspace can be completely filled with the liquid transdermal therapeutic preparation. Besides, after the skin and collar are to be fixed by the holder, the cap bulk is to be inserted into the through-hole of the holder to form an interspace. Then, liquid transdermal therapeutic preparation can be supplied through the interspace to form a liquid transdermal therapeutic layer.

Then, the diffusion testing cell (2) is placed into the notch and through-hole of metal block of the thermostat bath with the skin and transdermal therapeutic formulation on the upper side. And then the receptor chamber is to be completely filled with receptor liquid. Then, the determination method is same as that of the diffusion testing cell (1).

If the skin and transdermal therapeutic preparation are to be placed horizontally, although air bubbles are trapped under the surface of the skin after the diffusion testing cell is completely filled with receptor liquid, it is easier to remove air bubble just by tilting and shaking the diffusion testing cell because the receptor liquid outlet is opened at the upper part of the receptor chamber.

Next, the testing method of diffusivity of drug from transdermal therapeutic formulation with the diffusion testing device in this invention is to be explained when said diffusion testing cell (3) is applied.

Firstly, a stirrer is placed into the receptor chamber. The diffusion testing cell (3) is installed with the opening upwards. The skin and transdermal therapeutic formulation are temporarily fixed by the collar at the opening with the skin towards the receptor chamber. Then the skin, percutanesoun absorption preparation and the collar are fixed by the cap. Because the skin and percuatneous absorption formulation is temporarily fixed by the holder, rumple will not be appeared when the cap bulk is screwed onto the sidewall of the cell bulk.

Then the electrodes are connected to both of the transdermal therapeutic preparation which are emerged at the two openings. The diffusion testing cell (3) is to be placed into the notch and through-hole of metal block of the thermostat bath with the skin and transdermal therapeutic formulation on the upper side. Then the receptor chamber is to be completely filled with receptor liquid and under the action of current. The determination is carried out using a same method as diffusion testing cell (1) is used. Thus, the transdermal therapeutic experiment can be carried on by iontophoretic method.

If the skin and transdermal therapeutic preparation are to be placed horizontally, although air bubbles are trapped under the surface of the skin after the diffusion testing cell is completely filled with receptor liquid, it is easier to remove air bubble just by tilting and shaking the diffusion testing cell because the receptor liquid outlets are opened at the upper part of the first and second upper receptor chambers.

Effect of the Invention

The diffusion testing device in this invention is as defined above. Because there is no need to use water as temperature keeping media of the thermostat bath, there is no evaporation of the liquid media during determination; so that the diffusion testing device facilitates the determination of diffusivity of drug from transdermal therapeutic preparation over a long time.

BRIEF DESCRIPTION OF DRAWINGS

FIG. 3 (a) is the ichnography of one example of the thermostat bath. (b) is a section view of figure (a) from A to A.

FIG. 8 (a) is a front view of the holder; (b) is a rear view of the holder; and (c) is a side view of the holder.

REFERENCE NUMERALS

1. Diffusion testing cell.
2. Stirrer.
3. Receptor liquid reservoir.
4. Thermostat bath.
5. Stirring device.
6. Receptor liquid sampling device.
7. Pump.
8. Infusion tube.
9. Skin and transdermal therapeutic formulation.
10. Cell bulk.
11. Receptor chamber.
12. Receptor liquid outlet.
13. Receptor liquid inlet.
14. Aperture
15. Opening.
16. Rotation resist pin.
17. Partition board.
20. Cap.
21. Cap bulk.
22. Holder.
23. Collar.
31. Receptor liquid.
41. Heat preservation box.
42. Aluminum block.
43. Through-hole.
44. Plane heater.
45. Temperature regulator.

BEST MODE FOR CONVEYING OUT THE INVENTION

Figure 2:
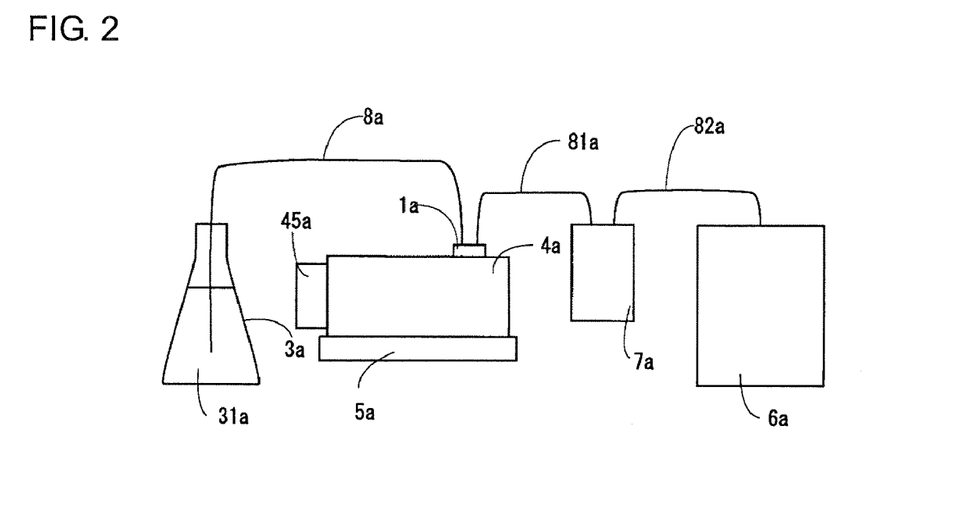
FIG. 2 is another example of the diffusion testing device in this invention.

Referring particularly to the drawing, the diffusion testing device for determination of the transdermal therapeutic preparation in this invention is explained. FIG. 1 is a model sample of the diffusion testing device for determination of transdermal therapeutic preparation in this invention. FIG. 2 is another model sample of the diffusion testing device for determination of transdermal therapeutic preparation in this invention.

In FIG. 1, receptor liquid reservoir 3 is to reserve receptor liquid 31. Receptor liquid reservoir 3 is connected with pump 7 to the infusion tube 8. The temperature of the thermostat bath 4 is regulated electrically by a temperature regulator 45 to be a specifically predetermined temperature level. The cuboids diffusion testing cell 1 is placed into a square apertures in the thermostat bath 4 to maintain the temperature at the certain level.

The stirring device 5 is installed beneath the thermostat bath 4 to cause the stirring action of the stirrer 2 within the receptor chamber. A stirring device for stirrers within the receptor chamber to rotate simultaneously is installed when a diffusion testing cell 1 is installed to determine the drug concentrations in cell at one time (for example, 12 consecutive stirrer to be used).

The receptor liquid inlet of the diffusion testing cell 1 connects pump 7 via infusion tube 81. The receptor liquid outlet of the diffusion testing cell 1 connects receptor liquid sampling device 6 via infusion tube 82. Then the components connect each other via infusion tube 8, 81 and 82 in following order: receptor liquid reservoir 3, pump 7, diffusion testing cell 1 and receptor liquid sampling device 6.

In FIG. 2, 3a is the receptor liquid reservoir to reserve receptor liquid 31. The temperature of the thermostat bath 4a is regulated electrically by a temperature regulator 45a to a specifically known temperature level. The cuboid diffusion testing cell 1a is placed in a square cylindrical aperture in the thermostat bath 4a to maintain the temperature at a certain level. Receptor liquid reservoir 3a is connected with receptor liquid inlet of the diffusion testing cell 1a by the infusion tube 8a.

5a is the stirring device installed beneath the thermostat bath 4a to cause rotation of the stirrer 2 within receptor chamber. Pump 7a connect both receptor liquid outlet of diffusion testing cell 1a and receptor liquid sampling device 6a via infusion tubes 81a and 82, respectively. Then the components connect each other via infusion tube 8a, 81a and 82a in following order: receptor liquid reservoir 3a, diffusion testing cell 1a, pump 7a and receptor liquid sampling device 6a.

Figure 3:
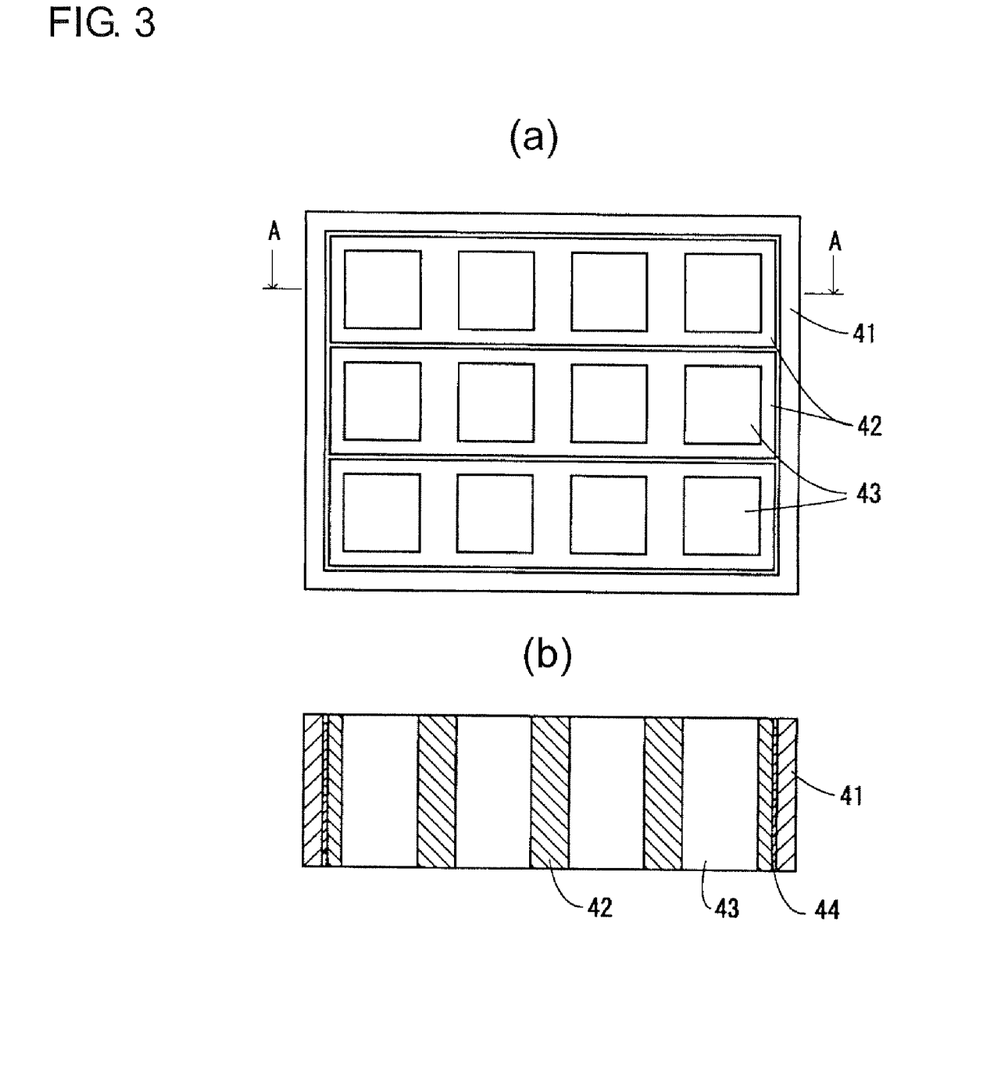

FIG. 3 (a) is a ichnography of thermostat bath. FIG. 3 (b) is the sectional view of FIG. 3 (a) from A to A. Referring to FIG. 3, 42 is the aluminium block with four square through-hole installed. The aluminium block 42 is winded by planar heater 44 all round. 41 is a Heat preservation box made from vinyl chloride resin in which three aluminium block 42 being installed. Planar heater 44 and temperature regulator 45 are electrically interconnected to form the thermostat bath 4.

Figure 4:
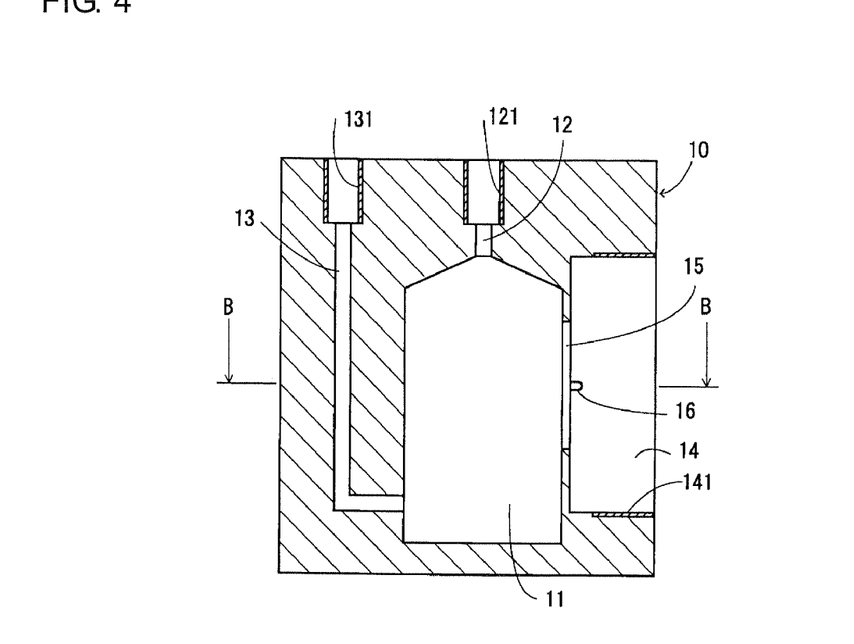
FIG. 4 is a longitudinal section of cell bulk.
Figure 5:
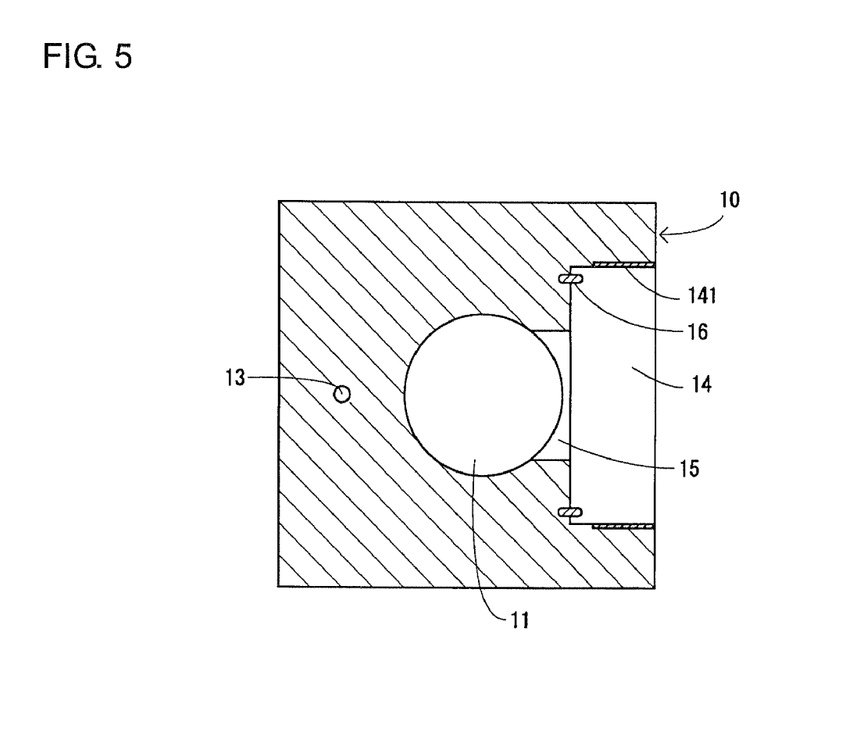
FIG. 5 is the sectional view of FIG. 4 from B to B.

FIG. 4 is a longitudinal section of cell bulk. FIG. 5 is the sectional view of FIG. 4 from B to B. Referring to FIG. 4 and FIG. 5, 10 is the cell bulk made from transparent hard vinyl chloride resin. Within the cell bulk 10, a receptor chamber 11 which is designed to be completely filled with receptor liquid is constructed. The cylindrical receptor chamber 11 has a smooth closed bottom and a trumpet-shaped top with a narrow end. The top end of the receptor chamber 11 connects to receptor liquid outlet 12. The outlet 12 has an open end connected to the upper wall of the cell bulk 10 and is to be expanded adjacent to the opening. The expanded part of the outlet 12 is spirally grooved 121.

Integrally connected to the lower sidewall of the receptor chamber is an receptor liquid inlet 13. The inlet 13 is opened at the upper wall of the cell bulk 10 and is to be expanded adjacent to the opening. The expanded part of the outlet 12 is spirally grooved 131.

14 is a aperture in shape of near circular from the side wall of cell bulk 10 towards receptor chamber 11 to fix cap bulk 21. The sidewall of the aperture 14 is spirally grooved 141. At the middle part of the side wall of receptor chamber 11, an opening 15 is designed towards the aperture 14 to set the skin and transdermal therapeutic preparation. To resist rotation of the holder 22, a rotation resist pin is designed at the bottom of the aperture 14.

Figure 6:
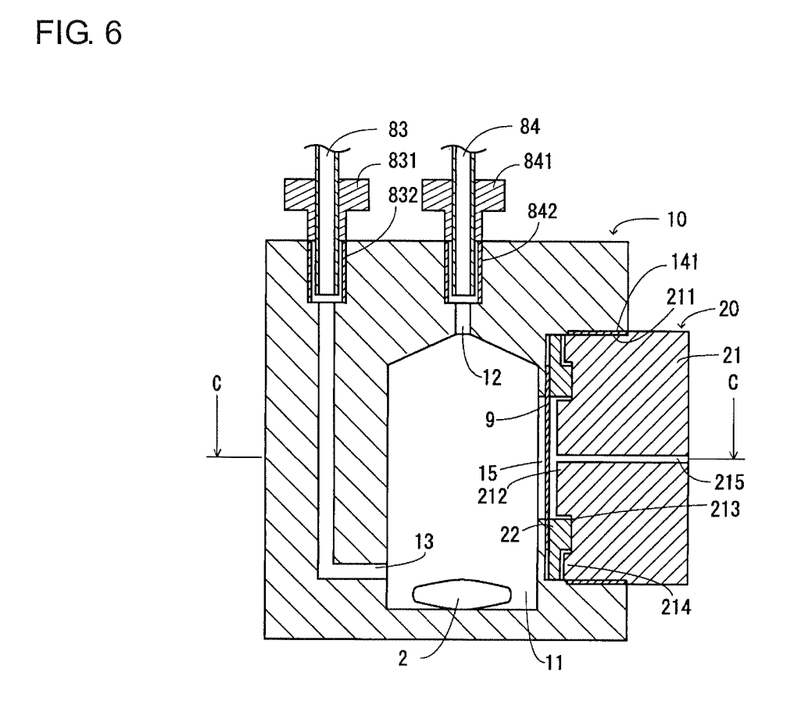
FIG. 6 is a longitudinal section of the diffusion testing cell in an example of the skin being stretched at the opening.
Figure 7:
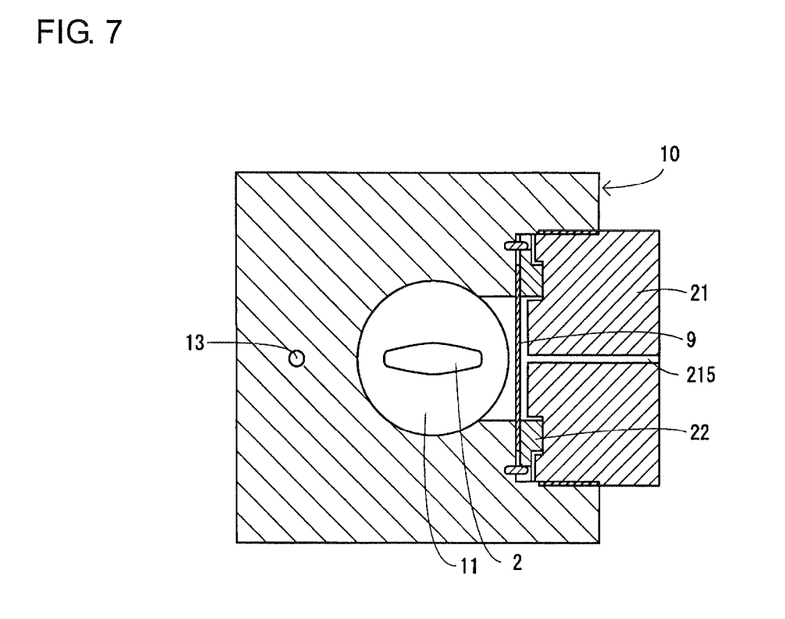
FIG. 7 is the sectional view of FIG. 6 from C to C.
Figure 8:
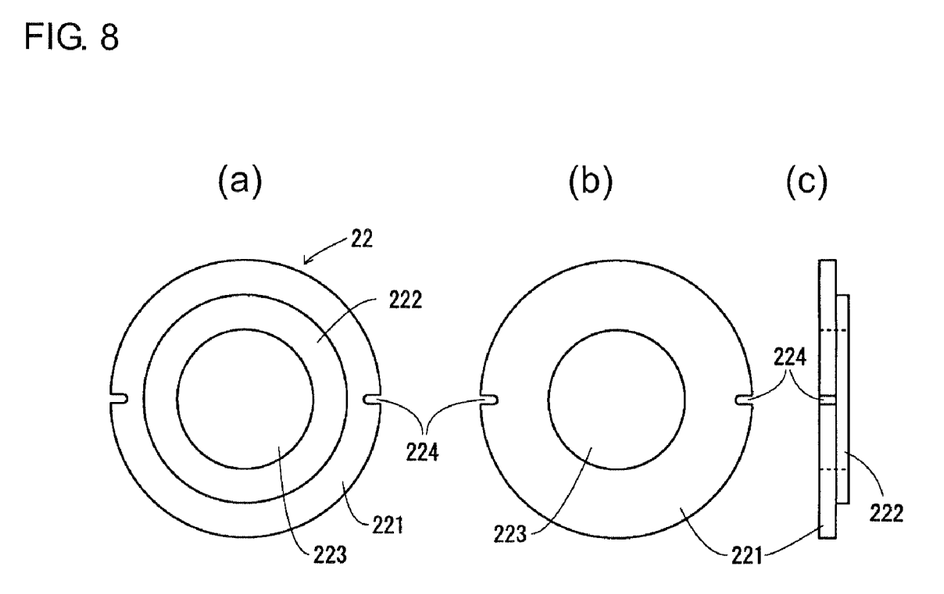

FIG. 6 is a longitudinal section of the diffusion testing cell in an example of the skin being stretched at the opening 15. FIG. 7 is the sectional view of FIG. 6 from C to C. FIG. 8 (a) is one of the examples of the front views of the holder. FIG. 8 (b) and FIG. 8 (c) are back view and side view of said holder, respectively.

Referring to FIG. 6 and FIG. 7, 20 is the cap which comprises a cap bulk 21 and a holder 22. In FIG. 8, it shows a nearly circular board-shaped body 221 in the front view of the holder 22. The size of the board-shaped body is almost the same as aperture 14 to make it possible to be inserted into the aperture 14. At the center of the board-shaped body 22, there is a centric through-hole 223 in almost the same shape as the opening 15. Around the centric through-hole 223, a centric flange 222 is constructed facing the cap bulk 21.

Cap bulk 21 is a cylindrical body with the spiral groove 211 surrounded. At its top end, it consecutively and centrically comprises a flange 212 which can be inserted into the through-hole 223 of the holder 22, an inter ledge 213 which can be inserted into the flange 222 of the holder 22 and a flange 214 which can be inserted into the recess around the flange 222 of the holder 22. Also, there is a through-hold 215 constructed through the near center of the cap bulk 21.

Skin and transdermal therapeutic preparation 9 are temporarily fixed in position of the opening 15 by the holder 22 at first, then they are firmly fixed by screwing the thread 211 of the cap bulk 21 onto the spiral groove 141 of the aperture 14. Between the skin and transdermal therapeutic preparation 9 as well as the top end there forms an interspace which is to be connected with outside via the through-hole 215 which is constructed in middle of the cap bulk 21.

If a fluidity preparation, such as gel, ointment, or jelly etc., is applied on the skin, it is desired that the interspace should be formed when the skin and preparation 9 is fixed and the air within the interspace can circulate with outside via the through-hole so as to prevent the evaporation of skin moisture which will result in incorrect determination of drug diffusivity.

83 is the infusion tube with the top end to be connected to an interface 831 which has spiral groove surrounded. By screwing the junction unit 831 onto the spiral groove of inlet 13 adjacent to the opening, infusion tube 83 and inlet 13 are water-tightly connected.

84 is the infusion tube with the top end to be connected to a junction unit 841 which has spiral groove surrounded. By screwing the junction unit 841 onto spiral groove 121 of outlet 12 adjacent to the opening, infusion tube 84 and outlet 12 are water-tightly connected. In addition, 2 is a stirrer to be located within the receptor chamber 11.

Figure 9:
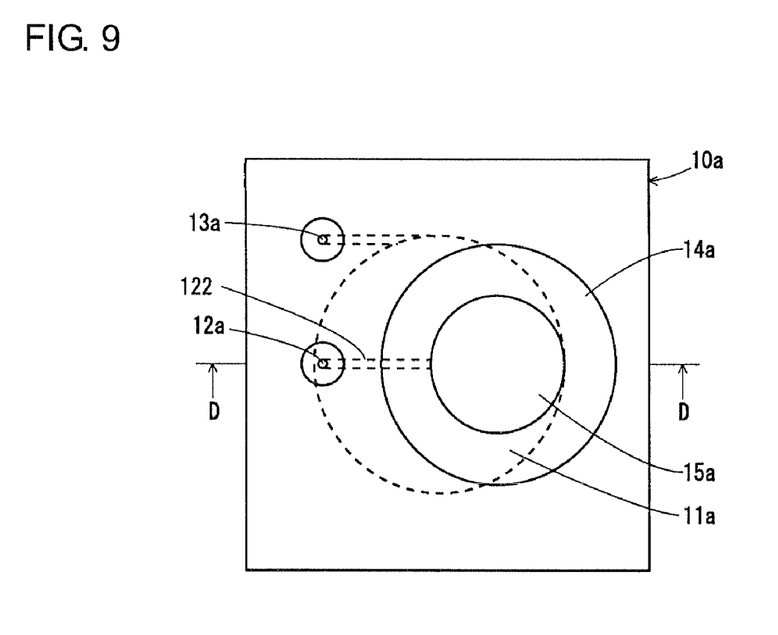
FIG. 9 is the different design of the cell bulk.
Figure 10:
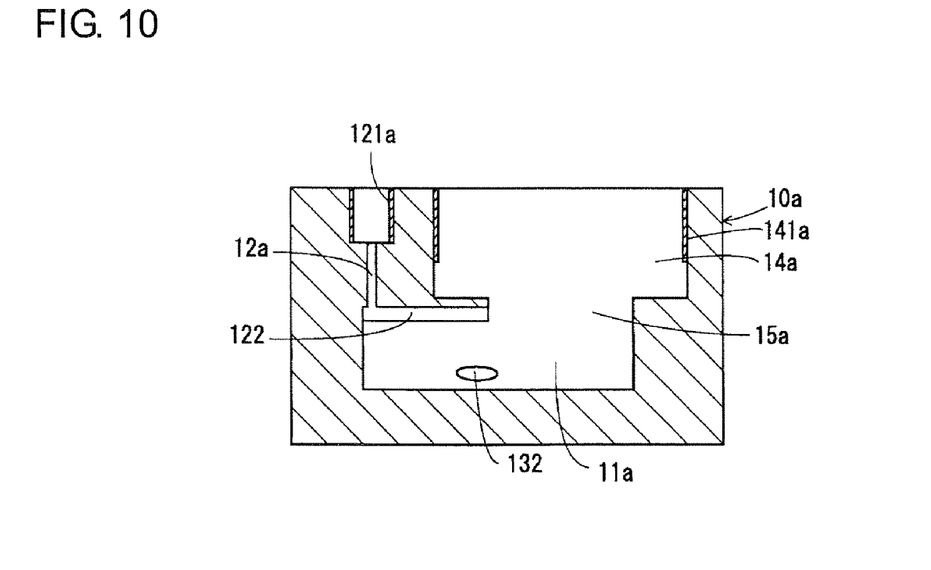
FIG. 10 is the sectional view of FIG. 9 from D to D.
Figure 11:
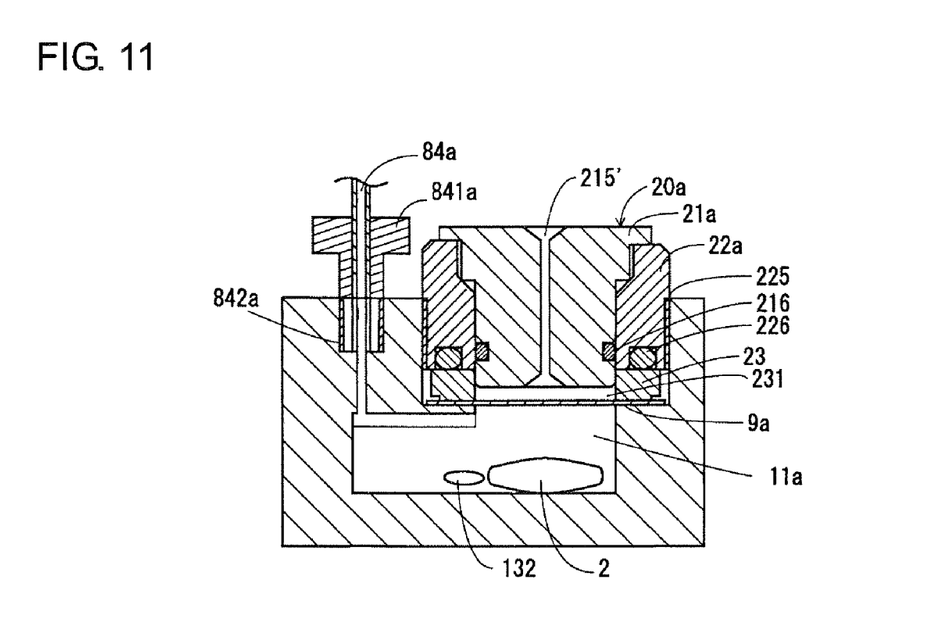
FIG. 11 is a sectional view of the cell bulk shown in FIG. 9 and FIG. 10 with skin being installed at the opening of the diffusion testing cell.

FIG. 9 is another example of ichnography of the cell bulk. FIG. 10 is a sectional view of FIG. 9 which is cut from D-D. FIG. 11 is a longitudinal section of the cell bulk shown in FIG. 9 and FIG. 10 in an example of the skin being stretched at the opening 15.

Referring to FIG. 9, FIG. 10 and FIG. 11, 10a is the cell bulk made from transparent hard vinyl chloride resin. Within the cell bulk 10a, a receptor chamber 11a which is to be full of receptor liquid is designed. 14a is a aperture in shape of near circular from the upper sidewall of cell bulk 10a towards receptor chamber 11a to fix cap 20a and collar 23. The sidewall of aperture 14 is threaded with spiral groove 141a. At top of the receptor chamber 11a, an opening with the size smaller than that of the aperture 14a is constructed and connected to the aperture 14a to be place with the skin and transdermal therapeutic preparation.

Integrally connected to the upper part of the receptor chamber is the receptor liquid outlet 12a. The lower end of the outlet 12a is connected to a aperture 122 which is formed at the upper wall of receptor chamber 11a from one part of the opening 15a to the end of the outlet 12a. In addition, outlet 12a is opened at the upper wall of the cell bulk 10a. The upper end of the outlet is to be broadened adjacent to the opening and is threaded with spiral groove. Because said aperture 122 is formed from one end of the opening 15a to the lower end of the outlet 12a, it is easier to remove air bubble just by tilting and shaking the diffusion testing cell if air bubbles are trapped under the surface of the skin after the diffusion testing cell is completely filled with receptor liquid.

The receptor liquid inlet 13a is connected to the side wall adjacent to the lower endwall of the receptor chamber 11a.

The opposite end of the inlet 13a is opened at the upper wall of the cell bulk 10a with the upper end being broadened and threaded with spiral groove. Besides, 132 is an opening of inlet 13a within the receptor chamber 11a.

23 is a tabular collar to temporarily fix the skin 9a. The collar 23a has the same through-hole to be constructed as the opening 15a. The size of the collar is almost the same as that of the aperture 14a to make sure that the collar can be inserted into the aperture 14a.

20a is the cap which comprises cap bulk 21a and holder 22a. The cylindrical holder 22a has the same through-hole to be constructed as the opening 15a and its diameter is almost the same as that of the aperture 14a. The collar has spiral groove 225 surrounded and can be fixed by screwing both the spiral grooves 225 and 141a. Besides, inner ledge with the rubber O-ring 226 to be inserted are formed at the bottom surface of the holder 22 to result in a water-tight connection between the holder 22a and the collar 23.

The cap bulk 21 a with a through-hole 215 to be constructed from the top end through to the lower end is a cylinder in almost the same shape as that of though-hole of the holder. At the top wall of the cap bulk 21a there formes an inner ledge to be inserted with a rubber O-ring 216 to result in a water-tight connection between the cap bulk 21a and the holder 22a. Besides, cap bulk 21a is broadened at its upper part and is of the length at least not to touch the skin 9a at its lower end when the cap bulk 21a is to be inserted into the through-hole of the holder 22a. Therefore, an interspace is formed among the cap bulk 21a, the holder 22a, collar 23 and skin 9a after the cap bulk 21a is to be inserted into the through-hole of the holder 22a. Liquid transdermal therapeutic preparation can be placed into the interspace to form the transdermal therapeutic preparation layer.

84a is the infusion tube with the top end to be connected to a junction unit 841a. The junction unit is threaded with spiral groove. By screwing the junction piece 841a onto the spiral groove 121a which is near the opening of outlet 12a, the infusion tube 84a and outlet 12a are water-tightly connected. Also, the inlet 13a for receptor liquid is threaded with spiral groove near its opening on. By screwing the spiral groove of the holder 13a onto the spiral groove of inlet 13a, infusion tube and inlet 13a can be water-tightly connected. Besides, a stirrer 2 is placed into the receptor chamber 11a.

Figure 12:
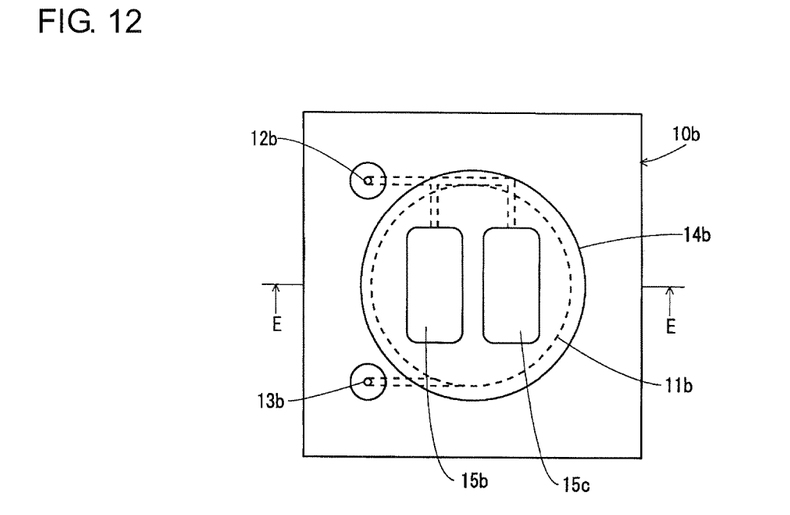
FIG. 12 is the ichnography o different cell bulk.
Figure 13:
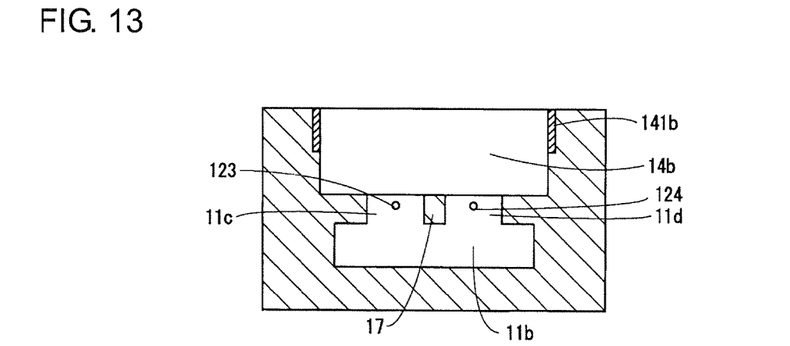
FIG. 13 is a sectional view of FIG. 12 from E to E.
Figure 14:
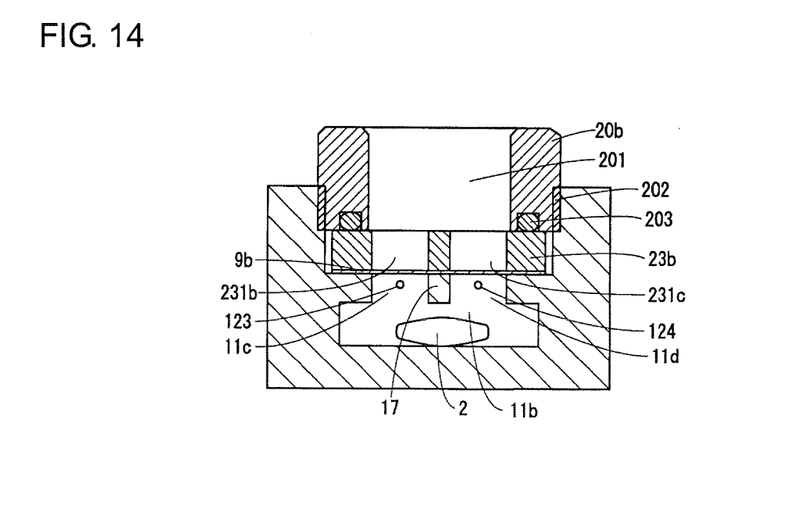
FIG. 14 is a sectional view of the cell bulk shown in FIG. 12 and FIG. 13 with skin being installed at the opening of the diffusion testing cell.

FIG. 12 is the planar view of another different example of the cell bulk. FIG. 13 is the sectional view being cut out from E to E. FIG. 14 is an example of the cell bulk shown in FIG. 12 and FIG. 13 but with skin and transdermal therapeutic preparation placed at the opening of the diffusion testing cell.

Referring to FIG. 12, FIG. 13 and FIG. 14, 10b is the cuboid cell bulk which is constructed of transparent hard vinyl chloride resin. Within the cell bulk, a cylindrical receptor chamber is designed to be completely filled with receptor liquid. A partition board in the upper chamber of the receptor chamber divides the receptor chamber into lower chamber 11b and first upper chamber 11c and second upper chamber 11d.

14b is a nearly cylindrical aperture which is designed from the upper sidewall of cell bulk 11b towards the first upper chamber 11c and second upper chamber 11d. The aperture 14b is cut with thread at its side-wall. In order to place the skin and transdermal therapeutic preparation, the nearly rectangular openings 15b and 15c are designed on top of the upper chambers 11c and 11d accordingly and are connected to the aperture 14b.

Above both the first and second upper receptor chambers lie and 11d is a receptor liquid outlet 12b which has an opening at top of the cell bulk and two openings 123 and 124 at its lower end connected to each upper part of the first and second upper receptor chambers 11c and 11d, respectively. The top opening is broadened at the upper part and thread with spiral groove. By screwing the spiral groove onto the infusion tube which has a junction unit threaded with spiral groove at the upper end, infusion tube and outlet 12b can be water-tightly connected.

Through the openings which are formed above each upper part of the first and second upper receptor chambers, 11c and 11d, it is easier to remove air bubble just by tilting and shaking the diffusion testing cell if air bubbles are trapped under the surface of the skin after the diffusion testing cell is full of receptor liquid.

Besides, a receptor liquid inlet 13b which is opened at both the upper wall of cell bulk and lower part of the receptor chamber 11b is designed. The opening of the inlet 13b at the upper wall of the cell bulk is threaded with spiral groove. By screwing the spiral groove onto the infusion tube which has a junction piece threaded with spiral groove at the upper end, infusion tube and inlet 13b can be water-tightly connected.

23b is a tabular collar to temporarily fix the skin 9b. The collar 23b comprises two through-holes of 231b and 231c which are in the near shape of opening 15b and opening 15c, respectively. The size of the collar is almost the same as that of the aperture 14b to make sure that the collar can be inserted into the aperture 14b.

20b is the cap which has a large enough through-hole to ensure the appearance of opening 15b and opening 15c at top of the cap 20b. The diameter of the cylindrical holder 20b is almost the same as that of the aperture 14b and is cut with thread 202 around and can be fixed by screwing the spiral groove 202 onto the spiral groove 141b of the aperture 14b. Besides, inner ledge with the rubber O-ring 203 to be inserted are threaded with spiral groove at the bottom surface of the cap 20b to result in a water-tight connection between cap 20b and collar 23.

Skin and percutaneosu absorption preparation 9b is temporarily fixed by collar 23b which is inserted into the opening 15b and opening 15c. Then, the skin and transdermal therapeutic preparation 9b is fixed by screwing the spiral groove 202 of the cap 20b onto the spiral groove 141 of the aperture 14. Besides, skin and percutaneosu absorption preparation 9b contact to ambient via the through-holes of 231b and 231c of the collar 23b and the through-hole 201 of cap 20b.

The invention claimed is:

1. A diffusion testing device for determination of transdermal therapeutic preparation determination comprising:
    a receptor liquid reservoir; a diffusion testing cell having a receptor chamber to be completely full of receptor liquid media, a stirrer being placed within said receptor chamber, a receptor liquid supply unit, a thermostat bath wherein said diffusion testing cell is placed, a stirring apparatus located beneath said thermostat bath to rotate said stirrer, a sampling unit permitting sampling and storage of receptor liquid dissolving permeated drugs, and a receptor liquid outlet disposed at an upper part of the diffusion testing cell; and said receptor liquid reservoir, said receptor chamber, said receptor liquid supply unit, and said sampling unit being connected via an infusion tube; and said thermostat bath comprising a metal block and apertures or through-holes within said metal block for admission of diffusion testing cell, said metal block having a temperature regulation unit installed.

2. The diffusion testing device for determination of transdermal therapeutic preparation determination as defined in claim 1, wherein:

a plurality of apertures or through-holes is designed within said thermostat bath.

3. The diffusion testing device for determination of transdermal therapeutic preparation determination as defined in claim 1, wherein:
said receptor liquid reservoir, said receptor liquid supply unit, said receptor chamber and said sampling unit are connected in order via infusion tube.

4. The diffusion testing device for determination of transdermal therapeutic preparation determination as defined in claim 1, wherein:
said receptor liquid reservoir, said receptor chamber, said receptor liquid supply unit and said sampling unit are connected in order via infusion tube.

5. The diffusion testing device for determination of transdermal therapeutic preparation determination as defined in claim 1, wherein:
said diffusion testing cell comprises a cell bulk, said cell bulk having an opening at the middle sidewall of said cell bulk to be placed with skin and transdermal therapeutic preparation, said cell bulk to be full of receptor liquid; within said cell bulk, a receptor liquid outlet connecting said receptor chamber from the upper part to outside of said cell bulk and a receptor liquid inlet connecting said receptor chamber from the lower sidewall to outside of said cell bulk being constructed.

6. The diffusion testing device for determination of transdermal therapeutic preparation determination as defined in claim 5, wherein:
a cap comprises a holder to keep the skin and transdermal therapeutic preparation at said opening and a cap bulk is pressed to fix said holder at said opening.

7. The diffusion testing device for determination of transdermal therapeutic preparation determination as defined in claim 5, wherein:
said receptor liquid outlet and inlet each have an upper end opening at the upper wall of said cell bulk.

8. The diffusion testing device for determination of transdermal therapeutic preparation determination as defined in claim 1, wherein:
a diffusion cell comprises a cell bulk, said cell bulk being formed with a receptor chamber to be full of receptor liquid, said receptor chamber having an opening at its upper sidewall to be placed with skin and transdermal therapeutic preparation; a collar to pre-fix said skin at said opening, a cap to press said collar tightly at said opening, said diffusion cell forming an interspace between said cap and said skin when said collar is fixed by said cap; within said cell bulk, a receptor liquid outlet connecting said receptor chamber from the upper part to outside of said cell bulk and a receptor liquid inlet connecting said receptor chamber from the lower sidewall to outside of said cell bulk being constructed.

9. The diffusion testing device for determination of transdermal therapeutic preparation determination as defined in claim 8, wherein:
said cap comprises a holder, said holder being pressed at said opening to fix said collar which possess a through-hole; a cap bulk being water-tightly embedded into said through hole of said holder.

10. The diffusion testing device for determination of transdermal therapeutic preparation determination as defined in claim 9, wherein:
said cap bulk has a through-hole from top to bottom of said cap bulk.

11. The diffusion testing device for determination of transdermal therapeutic preparation determination as defined in claim 8, wherein:
said receptor liquid outlet and inlet each have an upper end opening at the upper wall of said cell bulk.

12. The diffusion testing device for determination of transdermal therapeutic preparation determination as defined in claim 1, wherein:
said diffusion testing cell comprises a cell bulk having an opening at its middle sidewall and a receptor chamber functioning to be full of receptor liquid, skin and transdermal therapeutic preparation being placed at said opening; a collar functioning to pre-fix the skin and transdermal therapeutic preparation at said opening; and a cylindrical cap being pressed on said collar to fix said collar at said opening, said receptor chamber divided by a partition board in the upper chamber into lower receptor chamber and first upper receptor chamber and second upper receptor chamber, within both the first upper receptor chamber and second upper receptor chamber each formed said opening, said collar having two through-holes corresponding to said opening; a receptor liquid outlet which forms from the adjacent of upper part of said first and second receptor chamber to outside of the cell bulk and a receptor liquid inlet which forms from the adjacent of lower sidewall to outside of cell bulk being formed within said cell bulk.

13. The diffusion testing device for determination of transdermal therapeutic preparation determination as defined in claim 12, wherein:
openings of said receptor liquid outlet and said receptor liquid inlet are designed on top of said cell bulk.

14. The diffusion testing device for determination of transdermal therapeutic preparation determination as defined in claim 12, wherein:
one receptor liquid supply unit is connected to one diffusion testing cell; a plurality of receptor liquid supply units and diffusion testing cells being designed.

* * * * *